United States Patent [19]
Satoh

[11] Patent Number: 5,937,026
[45] Date of Patent: Aug. 10, 1999

[54] MICRO FLUORESCENT X-RAY ANALYZER

[75] Inventor: Masao Satoh, Chiba, Japan

[73] Assignee: Seiko Instruments Inc., Japan

[21] Appl. No.: 08/872,430

[22] Filed: Jun. 10, 1997

[30] Foreign Application Priority Data

Jun. 11, 1996 [JP] Japan ................................. 8-149280

[51] Int. Cl.[6] .............................................. G01N 23/223
[52] U.S. Cl. .............................................. 378/44; 378/45
[58] Field of Search ........................................ 378/44–50

[56] References Cited

U.S. PATENT DOCUMENTS 3,256,431  6/1966  Fraser ......................................... 378/47

FOREIGN PATENT DOCUMENTS

| 318012A2 | 5/1989 | European Pat. Off. . |
| 373656A2 | 6/1990 | European Pat. Off. . |
| 19515574A1 | 11/1995 | Germany . |
| 4444102C1 | 3/1996 | Germany . |

OTHER PUBLICATIONS

Nuclear Instruments and Methods in Physics Research, B13, 1996, pp. 122–127, Chevallier et al, "X–ray miroprobes". No month.

Nuclear Instruments and Methods in Physics Research, A302, 1991, pp. 547–552, Engstrom et al, "A submicron synchrotron X–ray beam generated by capillary optics". No month.

*Primary Examiner*—Craig E. Church
*Attorney, Agent, or Firm*—Adams & Wilks

[57] ABSTRACT

There is provided a structure wherein a detector for measuring the fluorescent X-rays is made into a thin and hollow cylindrical type configuration and this detector is fitted onto the vicinity of an end on the sample side of the X-ray capillary tube for decreasing primary X-rays to a thin flux.

20 Claims, 4 Drawing Sheets

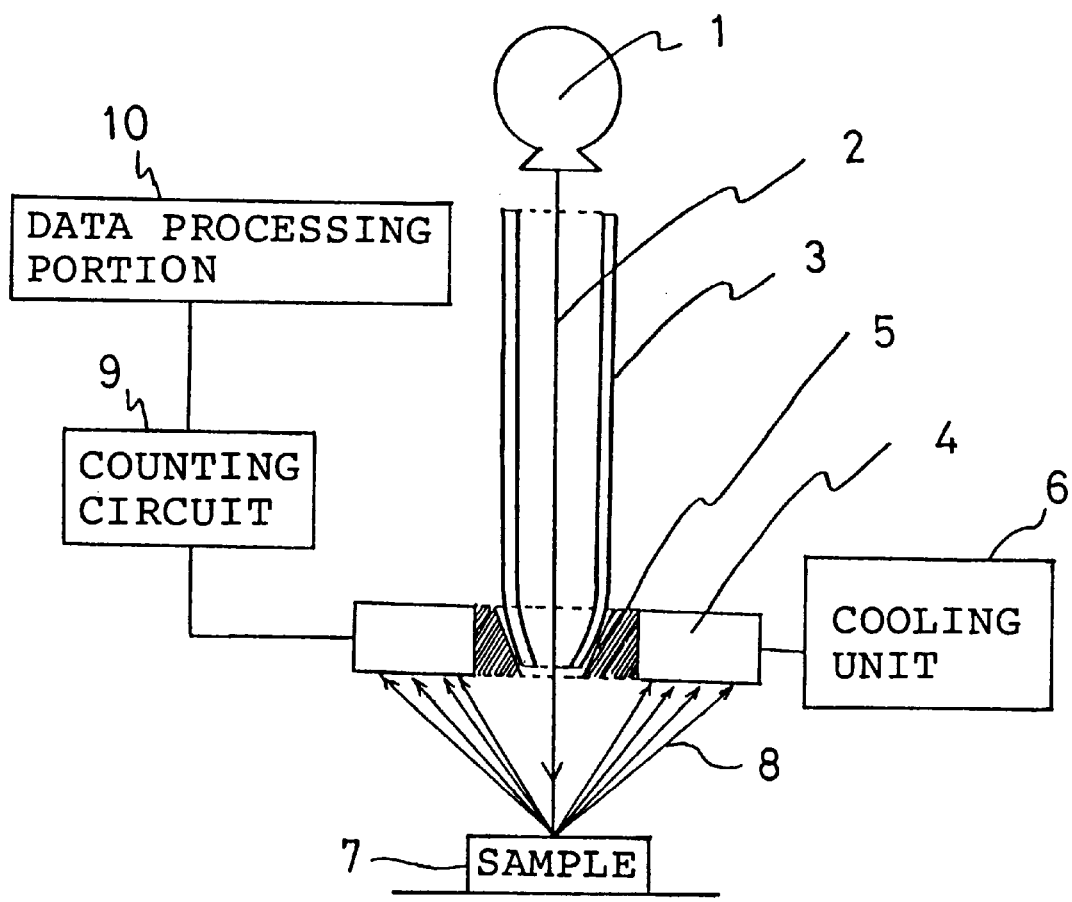

F I G. 2A
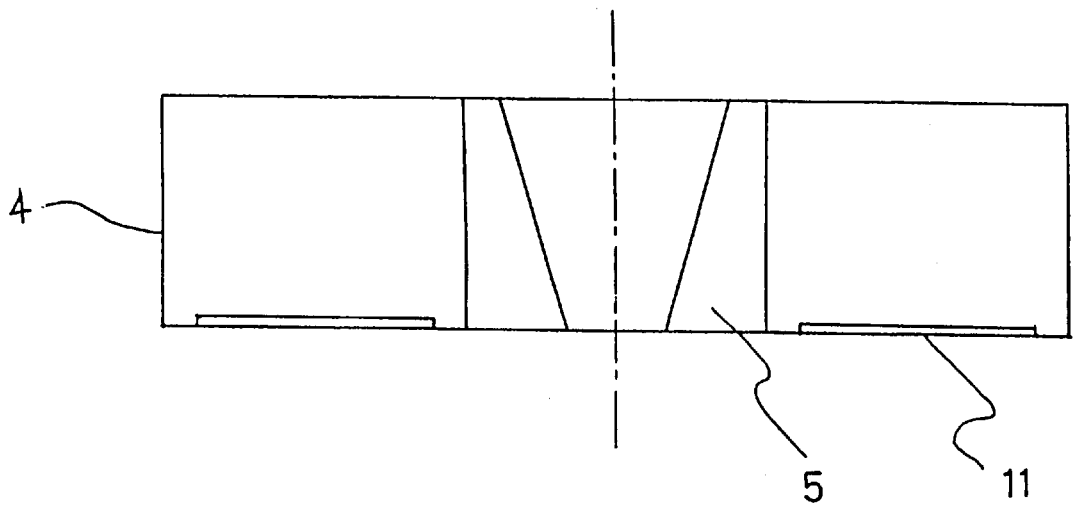
F I G. 2B
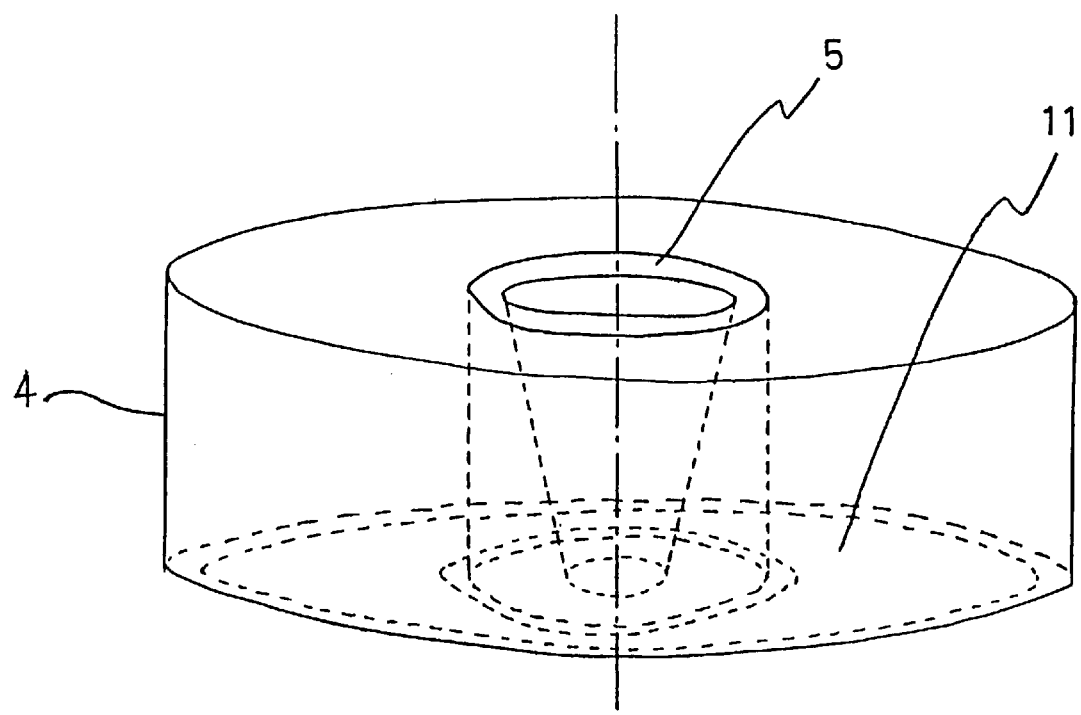

MICRO FLUORESCENT X-RAY ANALYZER

BACKGROUND OF THE INVENTION

The present invention relates to a micro fluorescent X-ray analyzing device for performing elemental analysis by making primary X rays into a thin flux and measuring fluorescent X rays that are generated from a fine region.

Concerning a conventional fluorescent analyzer, under the understanding that the region where primary X-rays are radiated is several tens of millimeters in diameter and the substances that exist in the world of nature have no uniformity as viewed in terms of their quality, measurement thereof is performed by the radiation area being widened to thereby perform averaging of such non-uniform qualities and thereby enhance the degree of accuracy. Under this circumstance, the KEVEX company in the United States: device name—Omicron and the TECHNO company in Japan: device name TREX 650 have recently developed fluorescent X-ray analyzing devices which are used for measurement in a region of the sub-millimeter order and which are called "micro fluorescent analyzing devices". FIG. 3 and FIG. 4 show the conventional micro fluorescent analyzing devices. In FIG. 3 and FIG. 4, 1 denotes an X-ray generating portion for generating primary X-rays, i.e. an X-ray tube, 2 denotes the primary X-rays that are generated from the X-ray tube, 3 denotes a capillary tube for restricting the primary X-rays into a high luminance of thin flux or a collimator of hollow metallic cylinder, 7 denotes a sample, 8 denotes fluorescent X-rays, 4 denotes a semiconductor detector which detects fluorescent X-rays 8, 6 denotes a cooling unit which cools semiconductor 4, 9 denotes a counting circuit for processing a signal of the fluorescent X-rays 8 that have been measured by the semiconductor detector 4, and 10 denotes a data processing portion for performing quantitative calculations, mapping display, etc. with respect to the measured data. In FIG. 4, 12 denotes an X-ray capillary tube (light receiving portion).

Also, while, conventionally, SEM-EDX or EPMA and XMA (X-ray m microanalysis) that utilize electronic microscopes were unavoidably forced to be applied to the elemental analysis or mapping analysis (distribution analysis) of a fine portion, since each of these analyses utilizes electron beams as the probe, such analyses involved therein the operational problems of necessitating the use of vacuum and of necessitating charge-up at a time of measurement of insulative material. By using X rays as the probe, there is the merit that the problem with insulative material can be settled. However, in the conventional micro fluorescent X-ray analyzing the devices, semiconductor detector 4 for measuring the fluorescent X-rays is formed into a probe configuration and is limited to unidirectional detection only. Accordingly, in order to approach the detector to the region from which the fluorescent X-rays are generated for the purpose of effectively measuring the intensity of a small amount of fluorescent X-rays, it is necessary to make small the forward end of the probe, i.e. detection area. However, when decreasing the detection area, the solid angle of detection of the fluorescent X-rays becomes small, with the result that there arises the problem of a sufficiently high level of intensity being not obtained. If the detection area is made large in order to make the solid angle large, the forward end of the probe becomes remote from the generation region of the fluorescent X-rays by reason of the structure and disposition, with the result that there arises the problem of a sufficiently high level of intensity being not obtained according to the inverse-square law of the distance.

Also, where fluorescent X-rays are measured from one direction, even if the primary X-rays are made into a thin flux with respect to a fine region, there arises the problem of the resulting fluorescent X rays inconveniently having a bias and broadening with directionality according to the detection angle. In the case of the X-ray analyzing device that is excited by electron beams, since electron beams cannot be deeply entered into because of having a certain value of weight and therefore have a short range that is of the sub $\mu$m order, the depth from which the X-rays are generated is several $\mu$m or less with the result that the X-rays are generated from the surface of a very small depth. Therefore, even when the detection angle exists, no difference is made within the fine region itself. However, since X-rays have a great power of transmission, even when the radiation area of X-rays on the surface of the sample is reduced to a value that is of the $\mu$m order, the depth from which the fluorescent X-rays are generated increases to a value that is of the order of several tens of $\mu$m to several mm although differing according to the coexistent elements. For this reason, in the case of the micro fluorescent X-ray analyzer, when detection is unidirectionally performed, there inconveniently arises the problem of bias and broadening.

On the other hand, there is also a technique wherein an X-ray capillary tube 12 shown in FIG. 4 is also disposed on the detection side in order to eliminate the effect of the broadening of the fluorescent X-rays that are generated from a fine region. However, in this case, because of the solid angle becoming too small, there was the problem that a sufficiently high level of detection intensity was not obtained.

The present invention has been made in order to solve the problems that are involved in the conventional micro fluorescent X-ray analyzer and provides a micro fluorescent X-ray analyzer that has been arranged to eliminate the effect of the bias and broadening with regard to the fluorescent X-rays that are generated from a fine region.

SUMMARY OF THE INVENTION

By making the configuration of the detector for measuring the fluorescent X-rays generated from a fine region into a hollow flat plate type, the X-ray capillary tube for making the flux of the primary X-rays thin can be disposed in the hollow portion of the hollow flat plate and can thereby be approached endlessly to a sample. In addition, the solid angle can be made large and the problem of directionality can also be solved. By making large the distance as measured from the sample with the solid angle being victimized, the broadening of the detection beams can be made small.

BRIEF DESCRIPTION OF THE DRAWINGS

FIG. 1 is a schematic view illustrating a micro fluorescent X-ray analyzer according to the present invention.

FIGS. 2A and 2B are views illustrating a hollow cylindrical type semiconductor detector that is used in the present invention.

DETAILED DESCRIPTION OF THE INVENTION

Figure 3:
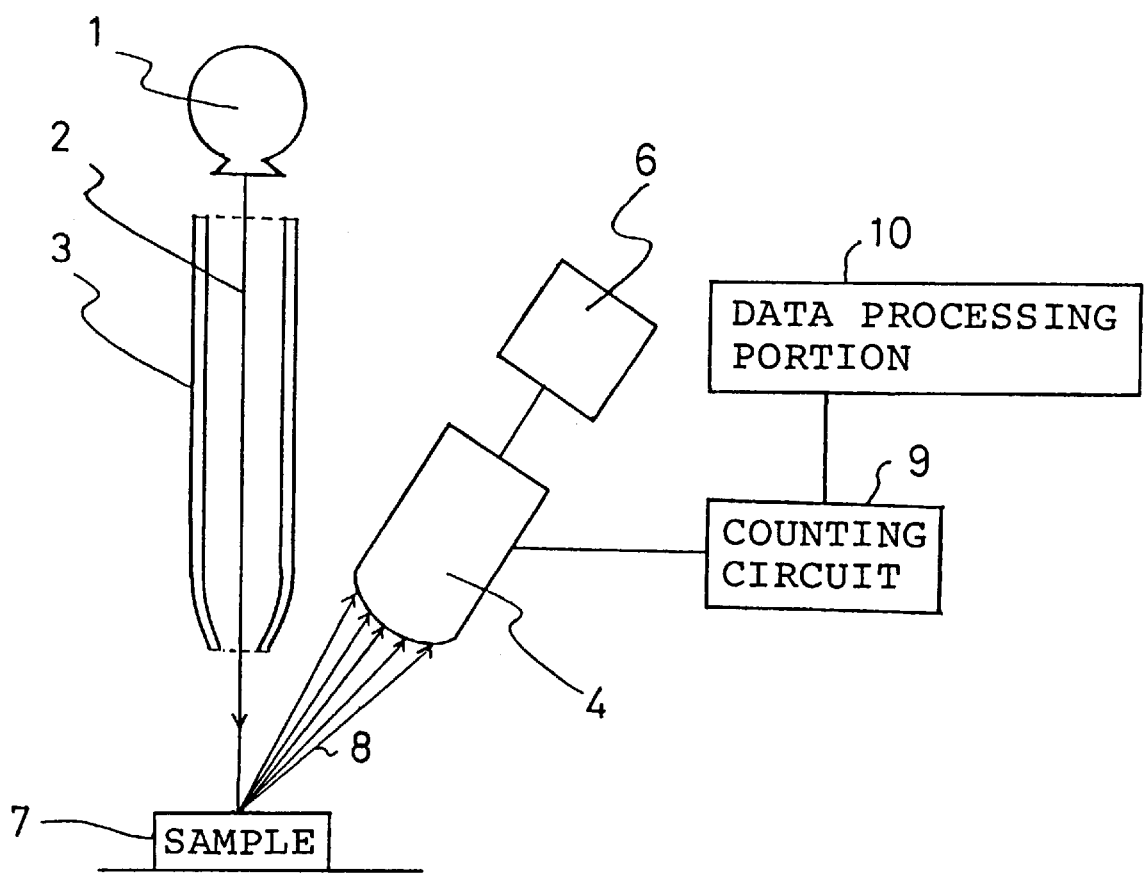
FIG. 3 is a schematic view illustrating a conventional micro fluorescent X-ray analyzer.
Figure 4:
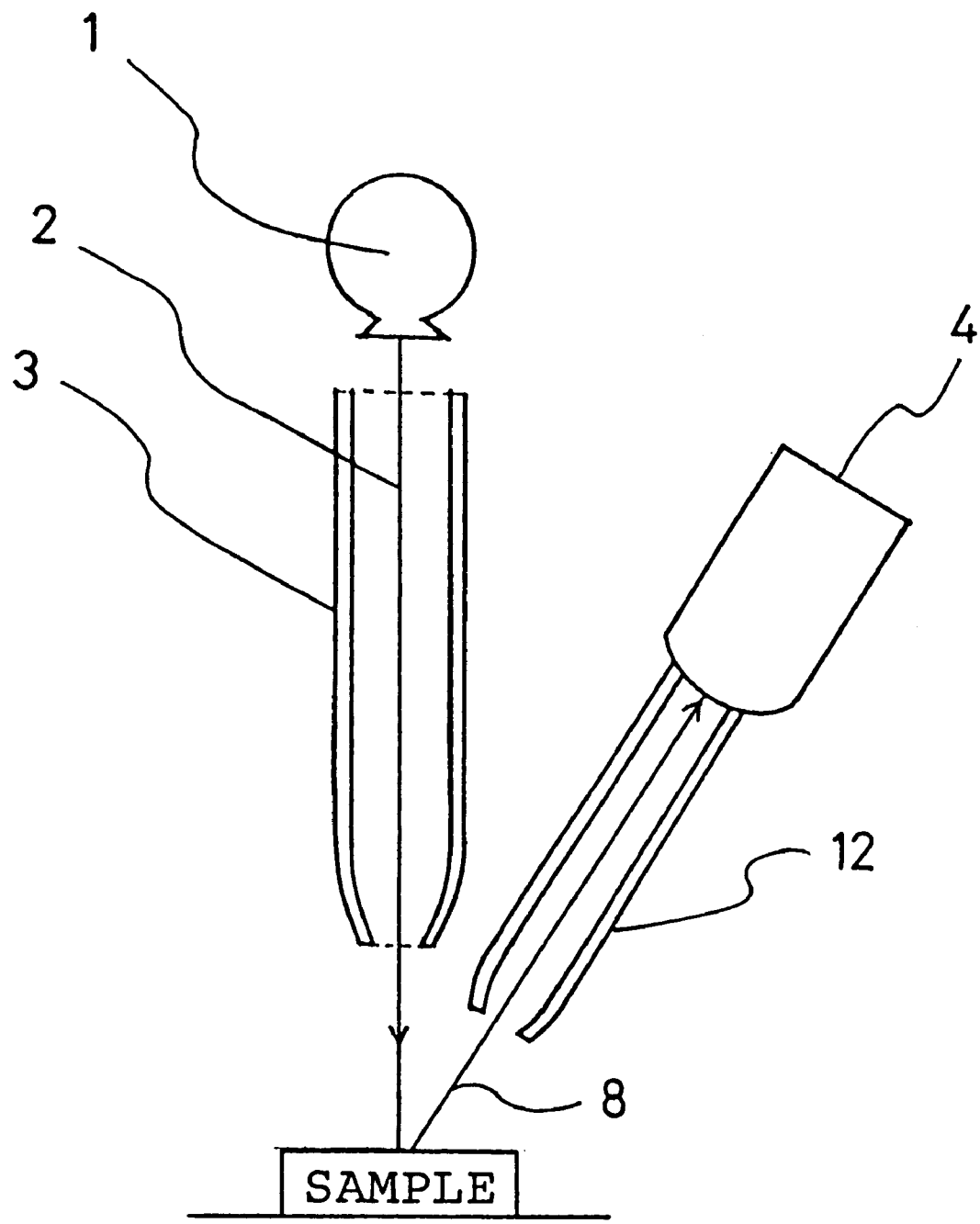
FIG. 4 is a schematic view illustrating another conventional micro fluorescent X-ray analyzer.

An embodiment of a micro fluorescent X-ray analyzer according to the present invention will now be explained with reference to the drawings.

An embodiment of the present invention is illustrated in FIG. 1

In the figure,

1 denotes an X-ray generating portion for generating primary X-rays, i.e. X-ray tube;

2 denotes the primary X-rays that are generated from the X-ray tube;

3 denotes a capillary tube for restricting or converting the primary X-rays into a narrow beam or thin flux of X-rays or a collimator formed of a hollow metallic cylinder for collimating the primary X-rays into a narrow beam or thin flux of X-rays;

4 denotes a semiconductor detector; and

5 denotes a collimator for making into a thin flux the high energy X rays that are transmitted on through the X-ray capillary tube 3, the collimator serving to shield the high energy X-rays which when the X-ray capillary tube is made of glass capillary leaks outside at the end thereof without being totally reflected.

6 denotes a cooling unit for realizing the operation of the semiconductor detector, or liquefied nitrogen;

7 denotes a sample to be measured;

8 denotes fluorescent X-rays that are generated from a fine region of the sample;

9 denotes a counting circuit for processing a signal of the fluorescent X-rays that have been measured by the semiconductor detector 4; and

10 denotes a data processing portion for performing quantitative calculations, mapping display, etc. with respect to the measured data.

The X-ray capillary tube 3 is a hollow capillary the configuration of which has been prepared by cutting one or each end of a circular cone member whose apex angle is two or less times as large as the X-ray total reflection critical angle, or the inner wall surface configuration of which is made cylindrical, and the inner wall surface of which is constituted by a smooth surface causing X-ray total reflection. The X-ray capillary tube 3 is needed to decrease the primary X rays down to a thin flux of the micron order and, if they are decreased down to a flux that is of the order of several tens of microns, they can be restricted also by a collimator after the X-ray capillary tube being demounted. FIG. 2A is a side view illustrating the semiconductor detector and FIG. 2B is a top perspective view taken from the top of FIG. 2A.

The semiconductor detector 4 is a thin type of circular disk plate and is of a hollow cylindrical type enabling the collimator 5 made of heavy metal to be embedded at the center thereof as illustrated in FIGS. 2A and 2B. This semiconductor detector 4 may be not always in the shape of a circular disk plate but, if it is hollow, maybe in the shape of an angular flat plate. One surface of the semiconductor detector 4 on the sample side has an X-ray detection window 11 that consists of a thin film of annular shape that is made of light element such as beryllium and, within the interior thereof, there is disposed a hollow cylindrical crystal such as silicon which has been compensated for by germanium, silicon and lithium. Namely, X-rays are transmitted through the hollow portion of the semiconductor detector 3 and the fluorescent X-rays that are generated from the sample onto which these X-rays have been radiated are detected by a detection portion located around the hollow portion. In order to process weak signals of the semiconductor detector, it is required to cool it at a super-low temperature. While this cooling was conventionally performed using liquefied nitrogen, since the semiconductor detector is of a thin hollow flat-plate type and therefore the portion to be cooled is the side of the flat plate, there is used a small-sized cooling unit 6.

While in the conventional X-ray analyzing devices even when the X-rays are decreased down to a thin flux the solid angle could not be made large because of limitation imposed on the disposition of the detector to raise the problem of the intensity decreasing with the distance or of beam broadening with directionality, according to the micro fluorescent X-ray analyzer of the present invention the detector is made into a hollow cylinder and the X-ray capillary tube is disposed at the center thereof, with the result that there can be brought about the excellent effects such as to enable close approach to the sample, to enable elimination of the directionality of the beam broadening and also to enable enhancement of the angle characteristic by detecting at an angle of 180° even when the surface of the sample has been inclined.

What is claimed is:

1. A micro fluorescent X-ray analyzer comprising: means including an X-ray capillary tube for radiating a thin flux of high luminance X-rays onto a fine region of a sample; and an energy dispersion type semiconductor detector for measuring fluorescent X-rays that are generated from the fine region of the sample, the semiconductor detector having a configuration of a hollow flat plate.

2. A micro fluorescent X-ray analyzer comprising: an X-ray generating portion for generating X-rays; an X-ray capillary tube for converting the X-rays from the X-ray generating portion into a narrow beam and radiating the narrow beam of X-rays onto a fine region of a sample; and a semiconductor detector for detecting fluorescent X-rays that are generated from the fine region of the sample upon radiation of the X-rays, the semiconductor detector comprising a hollow flat plate having a hollow portion and being so disposed that the narrow beam of X-rays passes through the hollow portion to radiate the sample.

3. A micro fluorescent X-ray analyzer as set forth in claim 1; further including a collimator comprised of heavy metal disposed on the semiconductor detector.

4. A micro fluorescent X-ray analyzer comprising: an X-ray generating portion for generating X-rays; a collimator for collimating the X-rays from the X-ray generating portion into a narrow beam and radiating the narrow beam of X-rays onto a fine region of a sample; and a semiconductor detector for detecting fluorescent X-rays that are generated from the fine region of the sample, the semiconductor detector comprising a hollow flat plate disposed on the collimator.

5. A micro fluorescent X-ray analyzer as set forth in claim 1; wherein the semiconductor detector comprises a hollow circular disk.

6. A fluorescent X-ray analyzer comprising: an X-ray source for generating X-rays; means for forming the X-rays into a narrow beam and radiating the narrow beam of X-rays onto a sample to cause the sample to emit fluorescent X-rays; and a semiconductor detector for detecting fluorescent X-rays emitted by the sample, the semiconductor detector having an opening therethrough through which the narrow beam of X-rays passes to radiate the sample, and a detecting portion surrounding the opening for detecting fluorescent X-rays emitted by the sample.

7. A fluorescent X-ray analyzer according to claim 6; wherein the detecting portion completely surrounds the opening.

8. A fluorescent X-ray analyzer according to claim 6; wherein the detecting portion has an annular configuration.

9. A fluorescent X-ray analyzer according to claim 6; wherein the means for forming the X-rays into a narrow beam comprises a capillary tube.

10. A fluorescent X-ray analyzer according to claim 9; wherein a forward end of the capillary tube extends into the opening of the semiconductor detector.

11. A fluorescent X-ray analyzer according to claim 10; wherein the means for forming the X-rays into a narrow beam further includes a collimator disposed in the opening of the semiconductor detector and surrounding the forward end of the capillary tube.

12. A fluorescent X-ray analyzer according to claim 11; wherein the collimator is composed of heavy metal.

13. A fluorescent X-ray analyzer according to claim 10; wherein the semiconductor detector comprises a flat plate.

14. A fluorescent X-ray analyzer according to claim 13; wherein the flat plate comprises a circular disk.

15. A fluorescent X-ray analyzer according to claim 6; wherein the means for forming the X-rays into a narrow beam comprises a tubular collimator.

16. A fluorescent X-ray analyzer according to claim 15; wherein a forward end of the tubular collimator extends into the opening of the semiconductor detector.

17. A fluorescent X-ray analyzer according to claim 16; wherein the semiconductor detector comprises a flat plate.

18. A fluorescent X-ray analyzer according to claim 17; wherein the flat plate comprises a circular disk.

19. A fluorescent X-ray analyzer according to claim 6; wherein the semiconductor detector comprises a flat plate.

20. A fluorescent X-ray analyzer according to claim 19; wherein the flat plate comprises a circular disk.

* * * * *